(12) United States Patent
Khoury

(10) Patent No.: US 8,070,806 B2
(45) Date of Patent: Dec. 6, 2011

(54) ACCOMMODATIVE INTRA-OCULAR LENS

(76) Inventor: Elie Khoury, Quebec (CA)

( * ) Notice: Subject to any disclaimer, the term of this patent is extended or adjusted under 35 U.S.C. 154(b) by 169 days.

(21) Appl. No.: 12/441,196

(22) PCT Filed: Sep. 17, 2007

(86) PCT No.: PCT/CA2007/001659
§ 371 (c)(1),
(2), (4) Date: Mar. 13, 2009

(87) PCT Pub. No.: WO2008/031231
PCT Pub. Date: Mar. 20, 2008

(65) Prior Publication Data
US 2009/0319040 A1  Dec. 24, 2009

(30) Foreign Application Priority Data
Sep. 16, 2006 (GB) ................................. 0618262.0

(51) Int. Cl.
*A61F 2/16* (2006.01)
(52) U.S. Cl. ..................... 623/6.13; 623/6.37
(58) Field of Classification Search ................ 623/6.13, 623/6.27, 6.24, 6.26, 6.37–6.39, 6.43, 6.46–6.47, 623/6.51–6.54
See application file for complete search history.

(56) References Cited

U.S. PATENT DOCUMENTS

| | | | |
|---|---|---|---|
| 4,253,199 A | 3/1981 | Banko | |
| 4,932,966 A | 6/1990 | Christie et al. | |
| 6,638,305 B2 | 10/2003 | Laguette | |
| 7,261,737 B2 * | 8/2007 | Esch et al. | 623/6.37 |
| 2005/0085906 A1 | 4/2005 | Hanna | |
| 2005/0137703 A1* | 6/2005 | Chen | 623/6.13 |
| 2006/0271186 A1 | 11/2006 | Nishi et al. | |
| 2007/0129801 A1 | 6/2007 | Cumming | |

OTHER PUBLICATIONS
International Search Report for PCT/CA2007/001659.
* cited by examiner

*Primary Examiner* — William H. Matthews
(74) *Attorney, Agent, or Firm* — Brooks Kushman P.C.

(57) ABSTRACT

An accommodative intra-ocular lens deformable between the unaccommodating and accommodating configurations upon the relaxation and contraction of the ciliary muscle. The lens anterior and posterior portions are substantially sealingly joined together about their peripheral edges and define a lens internal volume filled with a substantially incompressible lens internal fluid. Causing a variable internal fluid pressure exerted on the lens inner surfaces. The lens is configured such that radius of curvature of both the central and peripheral sections of the lens anterior portion will decrease upon an increase in internal fluid pressure and increase upon a decrease in internal fluid pressure.

12 Claims, 8 Drawing Sheets

FIG. 1

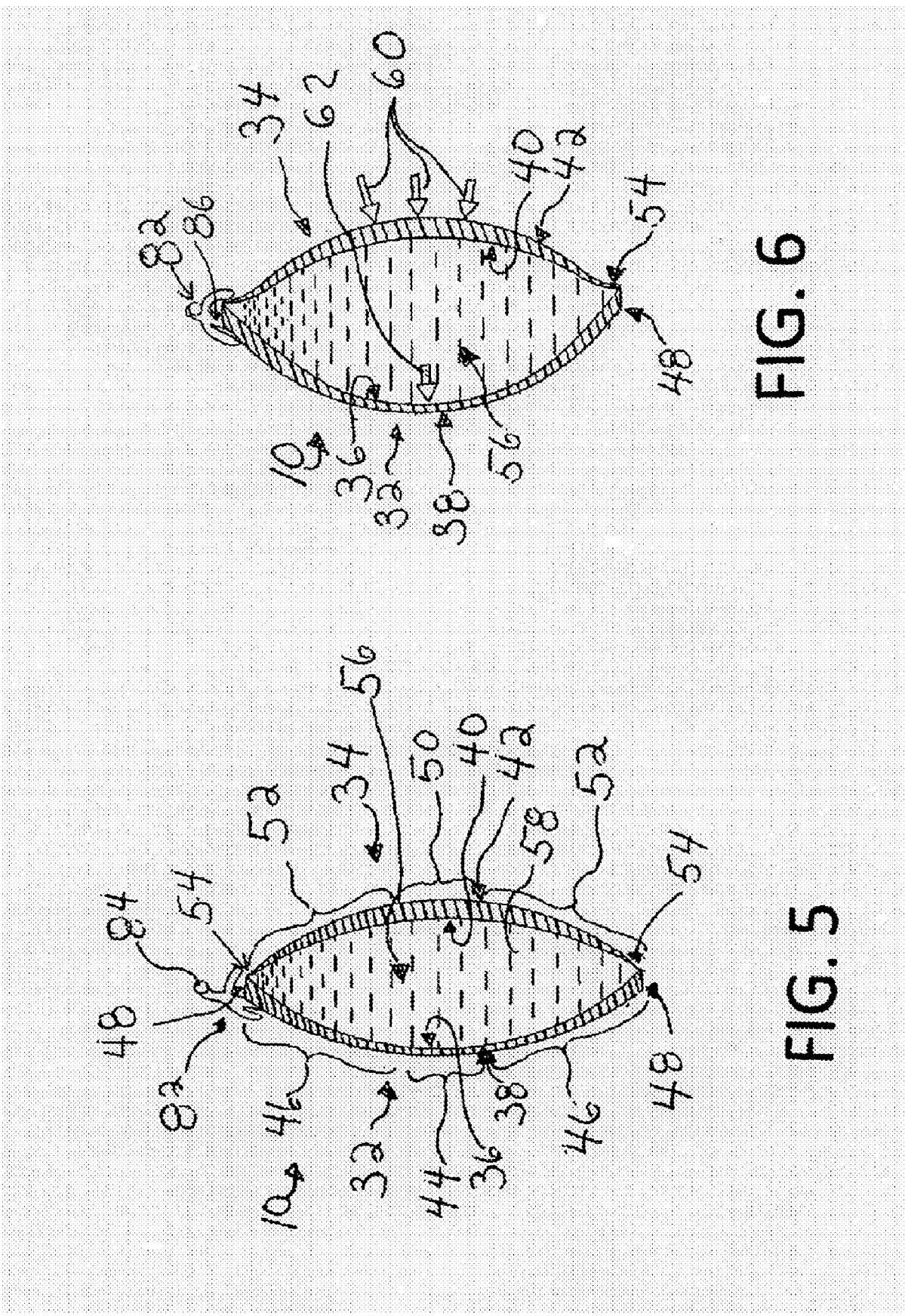

ACCOMMODATIVE INTRA-OCULAR LENS

FIELD OF THE INVENTION

The present Invention relates to the general field of intra-ocular lenses and is particularly concerned with an accommodative intra-ocular lens.

BACKGROUND OF THE INVENTION

As is well known, light enters the eye through the cornea. Besides serving as a protective covering for the front of the eye, the cornea also helps focus light on the retina located at the back of the eye. After passing through the cornea, light enters the pupil located In the middle of the iris.

Behind the iris sits the lens. The lens divides the eyeball of mammalian into two segments, each filled with fluid. The anterior segment extends from the cornea to the lens. The posterior segment extends from the back edges of the lens to the retina. The anterior segment itself is divided into two chambers. The anterior chamber extends from the cornea to the iris while the posterior chamber extends from the iris to the lens.

The anterior segment is filled with a fluid called the aqueous humor that nourishes its internal structures. The posterior segment contains a gel-like substance called the vitreous humor. These fluids help the eyeball maintain its shape.

The mammalian crystalline lens typically has a natural elasticity and, in its relaxed state, assumes a substantially bi-convex configuration wherein it has a generally circular cross-section of two convex refracting surfaces. Generally, the curvature of the posterior surface of the lens, i.e. the surface adjacent to the vitreous body, is somewhat greater than that of the anterior surface.

The lens is generally located on the optical axis of the eye, i.e. in a substantially straight line drawn from the centre of the cornea to the macula on the retina at the posterior portion of the globe. The lens is closely surrounded by a membranous capsule that serves as an intermediate structure in the support and actuation of the lens. The lens capsule has transparent elastic anterior and posterior walls or capsular membranes. The lens and its capsule are suspended on the optical axis behind the pupil by a circular assembly of cobweb-like and radially-directed collagenous fibers commonly referred to as the zonules, that are attached at their inner ends to the equatorial region of the lens capsule and at their outer ends to the ciliary body, a muscular ring of tissue located just within the outer supporting structure of the eye, known as the sclera.

By changing its shape, the lens focuses light onto the retina. Normally, the eye creates a clear image because the cornea and lens refract incoming light rays to focus them on the retina. The shape of the cornea is fixed, but the lens changes shape to focus on objects at various distances from the eye. The diopter value of a lens is defined as the reciprocal of the focal lens, i.e.:

$$\text{Diopter} = 1/\text{focal length (m)}$$

Focal length is the distance from the centre of the lens to the object being viewed. The focal length must decrease as magnification Increases. The diopter value expresses the refractive capacity of a lens which is associated with the radius of curvature of the optics. Generally, an increased diopter value indicates that the optic is thicker and also has a lesser radius of curvature, thus possessing greater light bending capability.

During a process known as accommodation, the shape of the lens is altered and, hence, its refractive properties thereby adjusted, to allow the eye to focus on objects at varying distances. A typical healthy eye has sufficient accommodation to enable focused vision on objects ranging in distance from infinity, which is generally defined as beyond 20 feet from the eye, to very near, i.e. typically closer than 10 inches.

Accommodation occurs when the ciliary muscle moves the lens from its relaxed or "unaccommodated" state to a contracted or "accommodated state". The ciliary body or muscle is relaxed in the unaccommodated eye and, therefore, assumes its largest diameter. When the viewer is observing an image located at a distance, the sensory cells within the retina signal the ciliary body to relax.

Accommodation occurs when the ciliary muscle moves the lens from its relaxed or "unaccommodated" state to a contracted or "accommodated" state. When the viewer is observing an image located at a distance, the sensory cells within the retina signal the ciliary body to relax. Conversely, the ciliary muscle is contracted in an effort for the eye to be focused on a near object.

Various accommodation theories have been proposed over the years. Probably, the most widely held theory of accommodation is that proposed by Helmholtz. According the Helmholtz theory, when focusing at near, the contraction of the ciliary muscle decreases the equatorial circumlenticular space. This, in turn, reduces the tension on the zonules and allows the lens to round up, hence increasing optical power. When viewing a distant object, the relaxation of the ciliary muscle increases the equatorial circumlenticular space causing an increase in zonular tension. The increase in zonular tension, in turn, causes the surfaces of the lens to flatten and the optical power of the lens to decrease.

According to the Schachar theory, while tension on equatorial zonules is increased during accommodation, the anterior and posterior zonules are simultaneously relaxing.

According to the Coleman theory, the lens, zonules and anterior vitreous comprise a diaphragm between the anterior and vitreous chambers of the eye. Ciliary muscle contraction initiates a pressure gradient between the vitreous and aqueous compartments that support the anterior lens shape in the mechanically reproducible state of a steep radius of curvature In the centre of the lens with slight flattening of the peripheral anterior lens, i.e. the shape, in cross-section, of a catenary.

According to Young, there is a pressure increase in the vitreous chamber under accommodation and convergence, and this increase in pressure is directly related to the amount of accommodation extended. Young feels that it is difficult to explain this pressure increase using the Helmholtz theory. A possibly more compatible explanation will be that of Tschering, claiming that the ciliary muscle, in pulling on the choroid, presses the vitreous, the ciliary body and the posterior part of the zonules against the lens, which is thus forcibly altered in shape.

According to Coleman, neither of these two theories of accommodation fully explains how the eye responds during accommodation. Coleman's model of the accommodative mechanism explains accommodation as a function of both lens plasticity and vitreous support based on analysis of hydraulic forces in the eye, showing that active vitreous support is consistent with decreased zonular tension and that the two theories are not contradictory.

The present invention takes into consideration the well-observed phenomena that there seems to be an increase in vitreous pressure during accommodation, possibly in relation with contraction of the ciliary muscle. Also, there seems to be a decrease in equatorial circumlenticular space upon muscle contraction.

Regardless of the theory, the natural accommodative capability thus involves contraction and relaxation of the ciliary muscles by the brain to alter the shape of the lens to the appropriate refractive parameters for focusing the light rays entering the eye onto the retina in order to provide both near and distant vision.

The natural accommodative capability thus involves contraction and relaxation of the ciliary muscles by the brain to alter the shape of the lens to the appropriate refractive parameters for focusing the light rays entering the eye on the retina in order to divide both near vision and distant vision.

There are multiple reasons for loss of accommodation. Typically, starting at age mid-40, a typical human eye begins to gradually lose its near distance vision, a process also referred to as presbyopia. One of the reasons is that the crystalline lens may become too hard to change back and forth from a thin lens to a thick lens.

The common approach for addressing such problem of loss of accommodation is to wear reading glasses. The prior art has also shown various attempts to solve presbyopia by implanting intra-ocular lenses.

Another conventional use for intra-ocular lenses is the replacement of the natural lens by an intra-ocular lens during cataract surgery. Indeed, in response to various physiological conditions, the most notable being the occurrence of cataracts, the natural crystalline lens may have to be removed and replaced by an intra-ocular lens.

The prior art discloses various examples of so-called monofocal intra-ocular lenses. Such monofocal intra-ocular lenses are produced with a single vision correction power, that being a vision correction power typically for distance vision. However, such conventional monofocal intra-ocular lenses typically do not provide sufficient near vision correction for reading or other situations where near vision is required.

The prior art also discloses so-called multifocal intra-ocular lenses that are produced with a lens providing more than one optical power, for example, a distance vision correction power and a near vision correction power. Although such multifocal intra-ocular lenses have proven to be relatively effective in providing the desired range of vision correction power, they may not be totally acceptable to some patients due to the simultaneous vision characteristics of such lenses which may produce halo and/or glare and/or decreased contrast sensitivity phenomena.

In order to provide patients with a range of vision correction powers with reduced risks of producing halo or glare phenomena, so-called accommodative intra-ocular lenses have been suggested in the prior art. Such prior art accommodative intra-ocular lenses may provide, for example, for the axial movement of the monofocal optic in order to vary the focus of an image on the retina. Most prior art accommodative intra-ocular lenses, however, suffer from some drawbacks.

For example, some prior art accommodative intra-ocular lenses are often limited by the amount of movement required to produce adequate accommodation.

Another problem encountered with the use of some prior art accommodative intra-ocular lenses is often referred to as posterior capsule opacification resulting from cell growth from the capsular bag unto the optics of the accommodative intra-ocular lens resulting from the presence of then latter. Such posterior capsule opacification can interfere with the clarity of the optic to the detriment of the vision of the lens wearer.

U.S. Pat. No. 4,253,199 to Banko approaches the problem of providing a focusable intra-ocular lens by providing a replacement intra-ocular lens of deformable material sutured to the ciliary body. This intra-ocular lens functions in much the same manner as the natural crystalline lens, but may cause bleeding because it requires sutures.

In an attempt to circumvent some of the problems associated with prior art lenses, U.S. Patent application Publication No. U.S. 2007/0129801 A1 naming J. Stuart Cummings as inventor and published Jun. 7, 2007 discloses an accommodative intra-ocular lens having an optic formed of solid silicone and liquid silicone. The optic is substantially circular and has a posterior portion of solid silicone extending into an anterior annular portion of solid silicone forming an outer diameter portion extending from the posterior side to an anterior side of the lens. The optic also includes a solid central anterior portion extending from the anterior annular portion which includes a membrane substantially thinner than the solid posterior and solid annular portions. The membrane is capable of deformation. The optic also includes a liquid silicone retained therein by the aforesaid solid portions. The optic is designed so that the anterior portion can change in radius of curvature upon an increase in vitreous cavity pressure on the posterior solid portion.

Although circumventing some of the problems associated with the prior art, the accommodative intra-ocular lens disclosed in this publication nevertheless suffers from some drawbacks. One of the main drawbacks associated with the structure disclosed in the Cumming application resides in the fact that the configuration of the anterior and posterior portions of the lens is such that the solid portions of the lens increase the risks that the latter creates refractive aberrations such as halo, glare and reduced contrast sensitivity. Indeed, for example, the configuration of the anterior portion of the lens is such that portions Identified respectively by the reference numerals 12b and 12d will deform substantially differently upon an increase in vitreous cavity pressure in part due to the relatively abrupt change in thickness at their juncture. The portions identified by the reference numerals 12a and 12b are designed so as to be sufficiently solid to prevent deformation of the optic upon implantation into the eye. This rigidity will also potentially contribute to the creation of refractive aberrations during use.

Against this background, there exists a need for an improved accommodative intra-ocular lens.

SUMMARY OF THE INVENTION

It is a general object of the present invention to provide such an improved accommodative intra-ocular lens.

Advantages of the present invention include that the proposed intra-ocular lens is specifically designed so as to provide a relatively large range of accomodation.

The proposed accommodative intra-ocular lens is also designed so as to provide relatively progressive accommodation.

Furthermore, the proposed accommodative Intra-ocular lens is designed so that the accommodation provided thereby can be controlled by the ciliary body of the eye and/or associated structures.

Yet, still furthermore, the proposed accommodative intra-ocular lens is designed so as to reduce the risk of creating refractive aberrations.

Also, the proposed accommodative intra-ocular lens is designed so as to substantially emulate or imitate the natural crystalline lens.

Furthermore, the proposed accommodative intra-ocular lens is designed so as to be relatively easily implantable through a set of conventional surgical procedures with reduced alteration of the eye portions.

Still furthermore, the proposed accommodative intra-ocular lens is designed so as to be manufacturable using conventional forms of manufacturing so as to provide an accommodative intra-ocular lens that will be economically feasible.

Yet, still furthermore, the proposed accommodative intra-ocular lens is designed so as to be relatively mechanically simple in order to provide a lens that will be reliable and able to maintain its properties through a relatively long life cycle.

In accordance with the present invention, there is provided an accommodative intra-ocular lens, the accommodative intra-ocular lens being deformable between an unaccommodating configuration and an accommodating configuration, the accommodative intra-ocular lens being implantable within a mammalian eye including a retina, a ciliary muscle, a vitreous chamber located posteriorly towards the retina relatively to the lens and a vitreous fluid contained within the vitreous chamber, the vitreous fluid defining a vitreous fluid pressure that increases upon contraction of the ciliary muscle and decreases upon relaxation of the ciliary muscle; the accommodative intra-ocular lens comprising: a lens first portion and a lens second portion for being positioned respectively anteriorly and posteriorly relative to each other when the accommodative intra-ocular lens is inserted in the mammalian eye; the lens first portion defining a first portion inner surface and an opposed first portion outer surface; the lens second portion defining a second portion inner surface and an opposed second portion outer surface; the lens first portion defining a substantially centrally disposed first portion central section and a first portion peripheral section extending radially from the first portion central section to a radially outwardmost first section peripheral edge; the first portion central and peripheral sections respectively defining a first central radius of curvature and a first peripheral radius of curvature; the lens second portion defining a substantially centrally disposed second portion central section and a second portion peripheral section extending radially from the second portion central section to a radially outwardmost second section peripheral edge; the second portion central and peripheral sections respectively defining a second central radius of curvature and a second peripheral radius of curvature; the lens first and second portions being substantially sealingly joined together about their respective first and second portion peripheral edges and configured so as to define a lens internal volume therebetween; the lens internal volume being filled with a substantially incompressible lens internal fluid; the lens internal fluid defining a variable internal fluid pressure exerted on the first and second portion inner surfaces; the accommodative intra-ocular lens being configured such that both the first central radius of curvature and the first peripheral radius of curvature will decrease upon an increase in internal fluid pressure and both the first central radius of curvature and the first peripheral radius of curvature will increase upon a decrease in internal fluid pressure; wherein the accommodative intra-ocular lens is deformable between the unaccommodating and accommodating configurations respectively upon the relaxation and contraction of the ciliary muscle.

In accordance with one embodiment of the invention, the lens second portion is configured so as to act as a resilient diaphragm for selectively increasing and decreasing the internal fluid pressure upon respectively an increase and a decrease of the vitreous fluid pressure; whereby the increase of the vitreous fluid pressure caused by the contraction of the ciliary muscle is transmitted, at least in part, to the lens internal fluid causing the lens first portion to deform towards the accommodated configuration and the decrease of the vitreous fluid pressure caused by the relaxation of the ciliary muscle is transmitted, at least in part, through the lens second portion to the lens internal fluid causing the lens first portion to resiliently deform towards the unaccommodated configuration.

In accordance with another aspect of the present invention, the first section peripheral edge includes a first portion outer surface peripheral edge; a first portion inner surface peripheral edge and a first end surface extending between the first portion outer surface peripheral edge and the first portion inner surface peripheral edge; the second section peripheral edge includes a second portion outer surface peripheral edge; a second portion inner surface peripheral edge and a second end surface extending between the second portion outer surface peripheral edge and the second portion inner surface peripheral edge; the first and second end surfaces being in a substantially face to face relationship relative to each other; the lens first and second portions are sealingly attached together about first and second portion peripheral edges by a portion attachment means that allows the lens first and second portions to selectively move relative to each other between a portion contacting configuration and a portion spaced configuration wherein the first and second end surfaces are respectively in a contacting and spaced relationship relative to each other; when the first and second end surfaces are spaced apart from each other, the lens internal volume includes a substantially annular peripheral volume portion extending between the first and second end surfaces, and a central volume portion extending radially centrally relative to the peripheral volume portion between the first and second portion inner surfaces; whereby when the lens first and second portions are moved towards the portion contacting configuration the volume of the lens internal fluid contained in the peripheral volume portion is compressed towards the central volume portion thereby increasing the overall pressure of the lens internal fluid and causing the accommodative intra-ocular lens to deform towards the accommodated configuration and, when the lens first and second portions are moved towards the portion spaced configuration the volume of the lens internal fluid contained in the central volume portion is resiliently compressed towards the peripheral volume portion thereby decreasing the overall pressure of the lens internal fluid and causing the accommodative intra-ocular lens to deform towards the unaccommodated configuration.

BRIEF DESCRIPTION OF THE DRAWINGS

FIG. 1 is an embodiment of the present invention implanted in the capsular bag of the eye in a non-accommodative state;

FIG. 5 is a section view of an embodiment of the present invention in a non-accommodative State;

FIG. 6 is a section view of an embodiment of the present invention in an accommodative state

DETAILED DESCRIPTION

Figure 1:
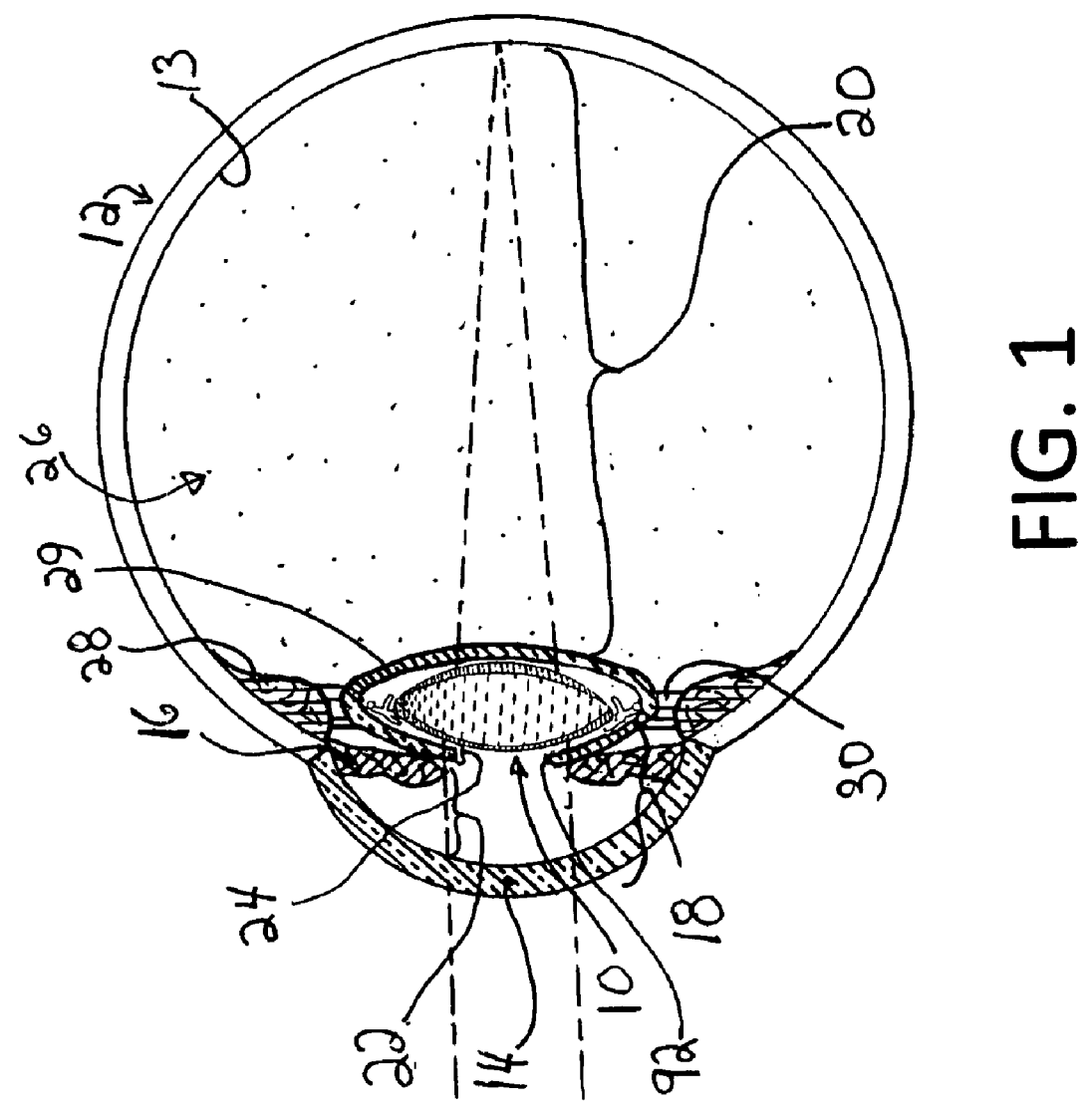
Figure 2:
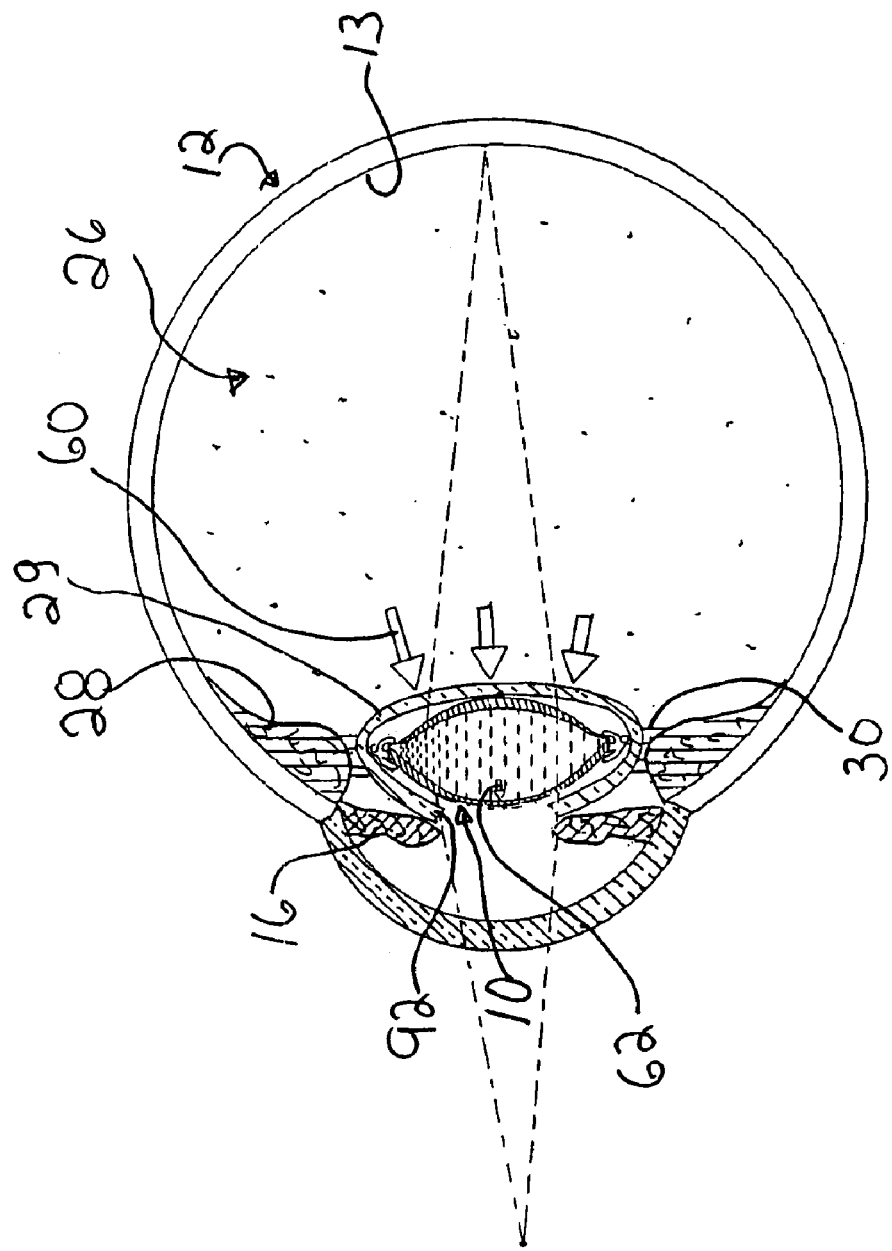
FIG. 2 is the embodiment of FIG. 1 in an accommodative state.

Referring to FIG. 1, there is shown an accommodative intra-ocular lens in accordance with an embodiment of the present invention, generally designated by the reference numeral 10 and herein referred to as an IOL. The OIL 10 is shown implanted in a mammalian eye schematically illustrated and generally referred to by the reference numeral 12.

As is well known, the eye 12 includes a cornea 14 and a pupil (not shown) located in the middle of the iris 16. Behind the iris 16 normally sits a crystalline natural lens (not shown) which has been replaced by the IOL 10.

The lens 10 divides the eye 12 into an anterior segment 18 extending from the cornea 14 to the lens 10 and a posterior segment 20 extending from the back edges of the lens 10 to the retina 13. The anterior segment 18, itself, is divided into an anterior chamber 22 extending from the cornea 14 to the iris 16 and a posterior chamber 24 extending from the iris 16 to the lens 10. The anterior segment 18 is filled with an aqueous humour while the posterior segment 20 contains a gel-like substance called the vitreous humour, generally designated by the reference numeral 26.

The vitreous fluid 26 contained in the posterior segment or vitreous chamber 20 defines a variable vitreous fluid pressure. The vitreous fluid pressure increases upon contraction of the ciliary muscle and decreases upon relaxation of the ciliary muscle.

FIGS. 1, 2, 7 and 8 also illustrate that the eye 12 typically also includes a ciliary muscle 28, portions of a capsular bag 29 and a so-called zonule 30 attached between the ciliary muscle 28 and portions of the capsular bag 29.

Figure 3:
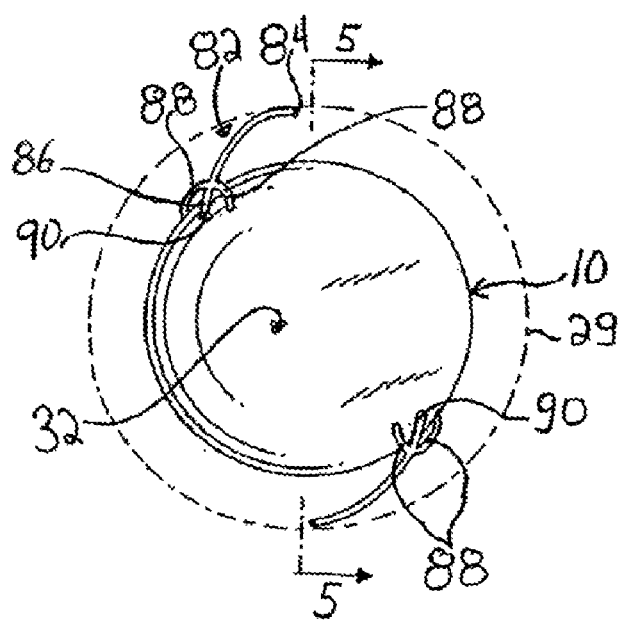
FIG. 3 is an anterior view of the embodiment with attached haptics.
Figure 4:
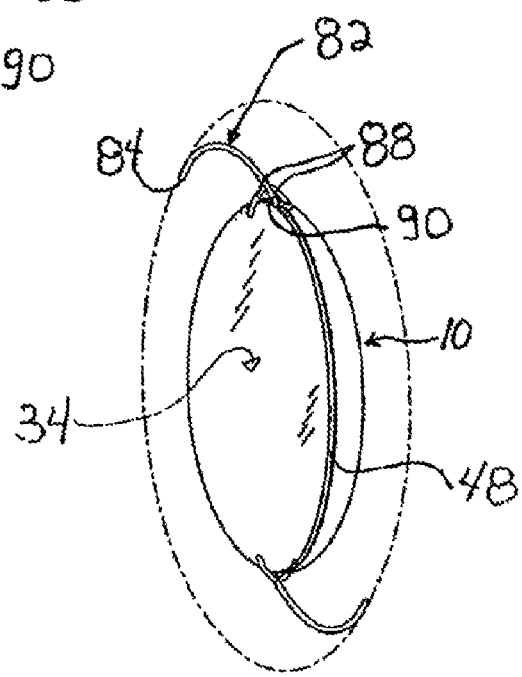
FIG. 4 is the embodiment of FIG. 3 in an oblique view.

Referring now more specifically to FIGS. 3 and 4, there is shown that the IOL 10 typically has a substantially bi-convex configuration. As shown more specifically in the cross-sectional views of FIGS. 5 and 6, the lens 10 includes a lens first portion 32 and a lens second portion 34 for being positioned respectively anteriorly and posteriorly relative to each other when the IOL 10 is inserted in the mammalian eye 12. The lens first portion 32 defines a first portion inner surface 36 and an opposed first portion outer surface 38. Similarly, the lens second portion 34 defines a second portion inner surface 40 and an opposed second portion outer surface 42.

The lens first portion 32 defines a substantially centrally disposed first portion central section 44 and a first portion peripheral section 46 extending radially from the first portion central section 44 to a radially outwardmost first section peripheral edge 48. The first portion central and peripheral sections 44, 46 respectively define a first central radius of curvature and a first peripheral radius of curvature.

Similarly, the lens second portion 34 defines a substantially centrally disposed second portion central section 50 and a second portion peripheral section 52 extending radially from the second portion central section 50 to a radially outwardmost second section peripheral edge 54. The second portion central and peripheral sections 50, 52 respectively define a second central radius of curvature and a second peripheral radius of curvature.

The lens first and second portions 32, 34 are substantially sealingly joined together about their respective first and second portion peripheral edges 48, 54 and configured so as to define a lens internal volume 56 therebetween, The lens internal volume 56 is filled with a substantially incompressible lens internal fluid generally indicated by the reference numeral 58. The lens internal fluid 58 defines a variable internal fluid pressure exerted on the first and second portion inner surfaces 36, 40.

The IOL is configured such that both first central radius of curvature and the first peripheral radius of curvature will decrease upon an increase in internal fluid pressure and both the first central radius of curvature and the first peripheral radius of curvature will increase upon a decrease in internal fluid pressure.

The IOL is of the accommodative type and is deformable between an unaccommodating configuration and an accommodating configuration. The IOL 10 is specifically designed so as to be deformable between the unaccommodating and accommodating configurations respectively upon the relaxation and contraction of the ciliary muscle 28.

Typically, the lens first portion 32 is configured such that both the first portion central section 44 and the first portion peripheral section 46 maintain a substantially catenary configuration when the lens first portion 32 is deformed between the unaccommodating and accommodating configurations. The first portion central section 44 is typically relatively more easily deformable than the first portion peripheral section 46.

The lens first portion 32 defines a first portion thickness extending between the first portion inner and outer surfaces 36, 38. The first portion thickness is preferably substantially smaller about the first portion central section 44 than about the first portion peripheral section 46.

The lens first portion 32 is designed so that the first portion thickness increases substantially gradually from the first portion central section 44 to the first portion peripheral edge 48. Preferably, the rate of variation of the first portion thickness is smaller than 350 microns of thickness variation per unit millimeter of displacement along the lens first portion 32. The gradual variation in thickness of the first portion 32 is adapted to reduce the risks of creating refractive aberrations such as halos, glare, reduced contrast sensitivity or the like and is in accordance with so-called "wave-front technology".

By way of example, the configuration of the lens first portion 32 may be approximated by that of a partial solid of revolution wherein the cross-sectional configuration of the first portion outer surface 38 corresponds substantially to the equation $y_o = \text{Log}_e(r_o^2 - x_o^2)^{0.5}$ wherein $r_o$ has approximately half the diameter value of the Intra-ocular lens;

$x_o$ is a variable having a value where $r_o^2 - x_o^2 \geq 1$ and is determining an ordinate value of a locus of the cross-sectional configuration of the first portion outer surface 38;

$y_o$ is a variable determining an abscissa value of a locus of the cross-sectional configuration of the first portion outer surface 38 and the cross-sectional configuration of the first portion inner surface 36 corresponds substantially to the equation $y_i = \text{Log}_e (r_i^2 - x_i^2)^{0.5}$ wherein $r_i$ has a smaller value than $r_o$ where $\text{Log}_e r_o - \text{Log}_e r_i$ represent the first portion central section 44 thickness;

$x_i$ is a variable having a value where $r_i^2 - x_i^2 \geq 1$ and is determining an ordinate value of a locus of the cross-sectional configuration of the first portion inner surface 36;

$y_i$ is a variable determining an abscissa value of a locus of the cross-sectional configuration of the first portion inner surface 36.

The lens second portion 34 is configured so as to act as a resilient diaphragm for selectively increasing and decreasing the internal fluid pressure upon respectively an increase and a decrease of the vitreous fluid pressure.

Typically, the second portion peripheral section 52 is relatively more easily deformable than the second portion central section 50. The lens second portion 34 defines a second portion thickness extending between the second portion inner and outer surfaces 40, 42. Typically, the second portion thickness is substantially smaller about the second portion peripheral section 52 than about the second portion central section 50.

Preferably, the second portion thickness increases substantially gradually from the second portion peripheral edge 54 to the second portion central section 50. Typically, the rate of variation of the second portion thickness is smaller than 350 microns of thickness variation per unit millimeter of displacement along the lens second portion 34.

FIG. 2 illustrates a situation wherein the ciliary muscle 28 is contracted. The contraction of the ciliary muscle 28 causes an increase in the vitreous fluid pressure. This increase in the vitreous fluid pressure is schematically represented by arrows 60. The lens second portion 34 is adapted to transmit, at least in part, through its deformation, the increase in vitreous fluid pressure to the lens internal fluid 58. Typically, the increase in vitreous fluid pressure is exerted on the second portion outer surface 42 causing the lens second portion 34 to generally move substantially anteriorly towards the lens first portion 32.

The increase in vitreous fluid pressure indicated by the arrows 60 is hence transmitted via the lens second portion 34 to the lens internal fluid 58. The increase in internal fluid pressure is indicated schematically in FIGS. 2 and 6 by arrows 62. This increase in internal fluid pressure, in turn, is adapted to cause the deformation of said lens first portion 32 towards the accommodated configuration.

Conversely, as illustrated in FIGS. 1 and 5, the decrease of the vitreous fluid pressure caused by the relaxation of the ciliary muscle 28 allows both the lens first and second portions 32, 34 to resiliently spring back to their unaccommodated configuration.

In use, the 10 is adapted to be implanted in the eye 12 and maintained in proper alignment therein by suitable lens fixing means such as conventional haptics 82 of the like that may or not be manufactured integrally with the IOL 10.

Referring now to FIGS. 7 through 12, there is shown an IOL 10' in accordance with a second embodiment of the invention, the IOL 10' is substantially similar to the IOL 10 and, hence, similar reference numerals will be used to denote similar components.

Figure 7:
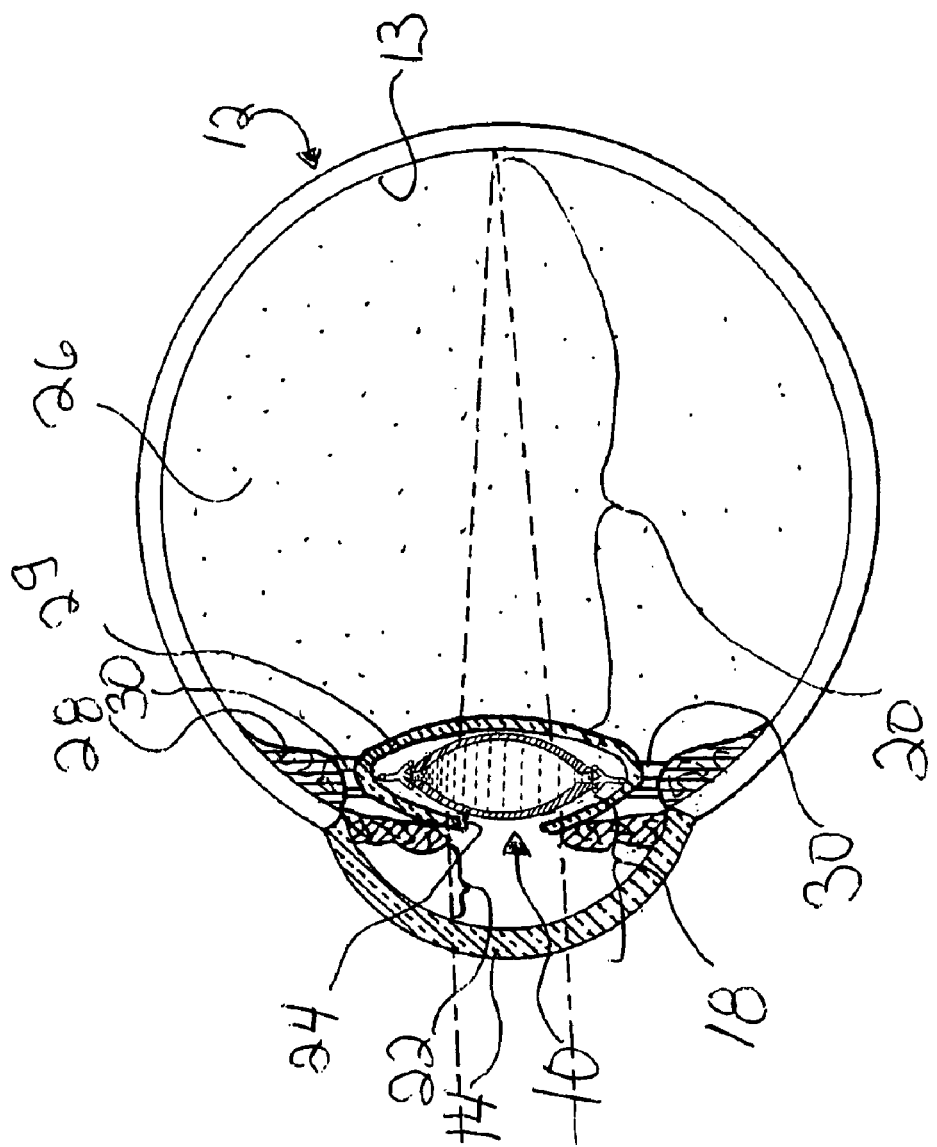
FIG. 7 is a second embodiment of the present invention implanted in the capsular bag of the eye in a non-accommodative state.
Figure 8:
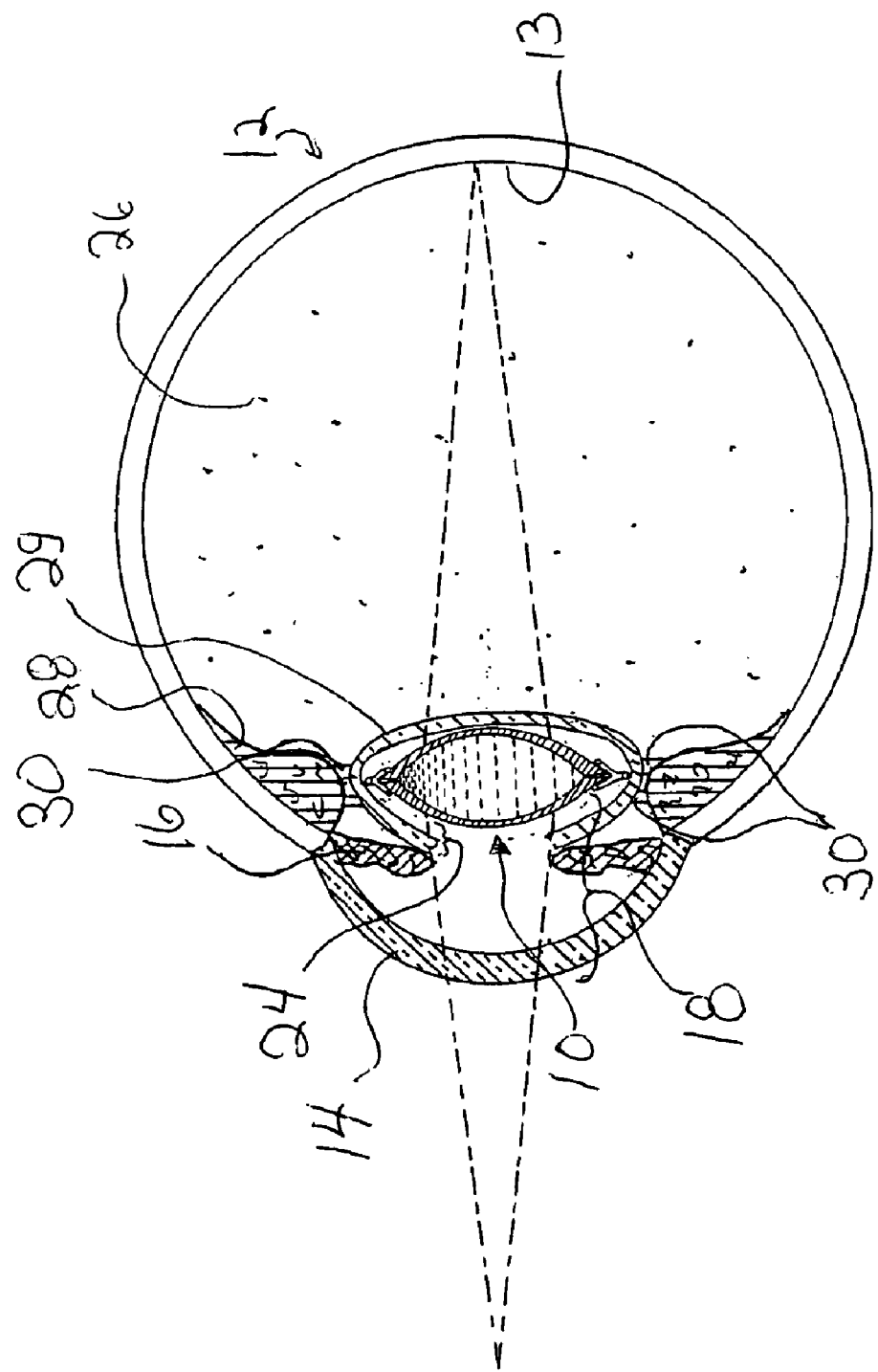
FIG. 8 is the embodiment of FIG. 7 in an accommodative state.
Figure 9:
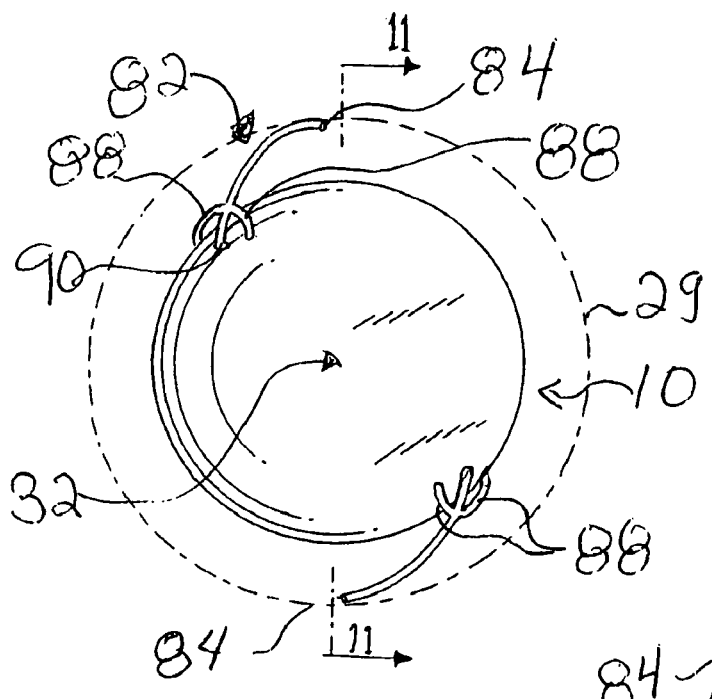
FIG. 9 is an anterior view of the second embodiment with attached haptics.
Figure 10:
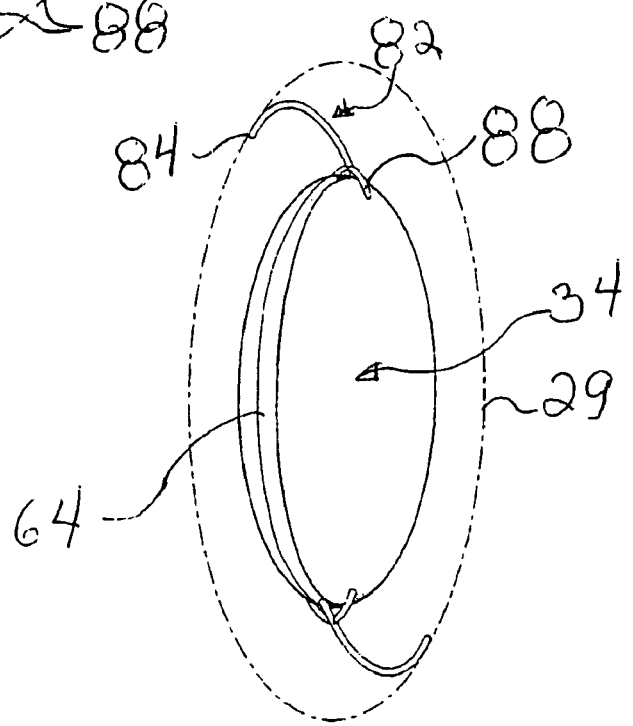
FIG. 10 is the second embodiment of in an oblique view.
Figure 12:
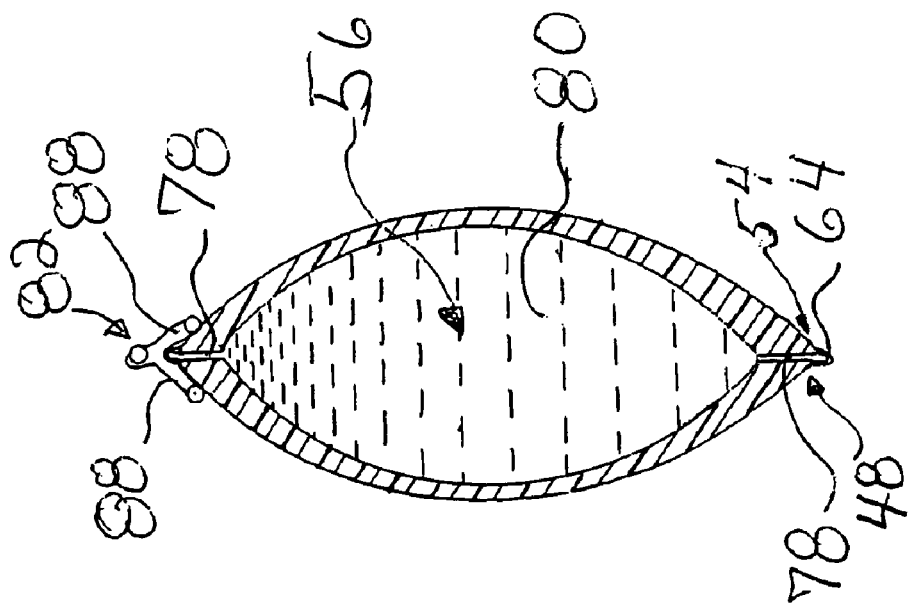
FIG. 12 is a section view of the second embodiment of the present invention in an accommodative state.
Figure 11:
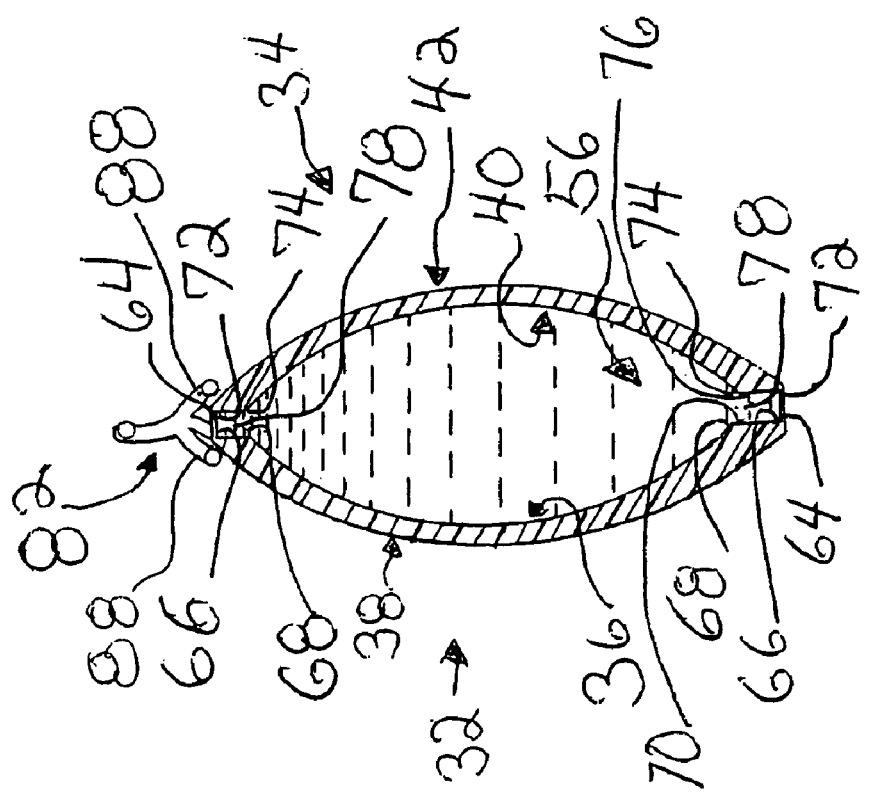
FIG. 11 is a section view of the second embodiment of the present invention in a non-accommodative state.

One of the main differences between the IOL 10' and the IOL 10 is that the lens first and second portions 32, 34 of the IOL 10', instead of being fixedly attached together, are attached together about their first and second portion peripheral edges 48, 54 by a portion attachment means that allows the lens first and second portions 32, 34 to selectively move relative to each other between a portion contacting configuration shown in FIGS. 8 and 12 and a portion spaced configuration shown in FIGS. 7 and 11. Preferably, the portion attachment means includes an equatorial attachment membrane 64 extending between the first and second section peripheral edges 48, 54.

Another difference between the IOL 10 and the IOL 10' typically resides in that the lens first and second portions 32, 34 are typically mirror images and typically both have a configuration wherein their respective first and second portion central sections 44, 50 are relatively more easily deformable than their respective first and second portion peripheral sections 46, 52. Typically, the first and second portion thicknesses are substantially smaller about their respective first and second portion central sections 44, 50 than about their respective first and second portion peripheral sections 46, 52.

Furthermore, the IOL 10' in accordance with the second embodiment of the present invention, the first section peripheral edge 48 includes a first portion outer surface peripheral edge 66, a first portion inner surface peripheral edge 68 and a first end surface 70 extending between the first portion outer surface peripheral edge 66 and the first portion inner surface peripheral edge 68.

Similarly, the second section peripheral edge 54 includes a second portion outer surface peripheral edge 72, a second portion inner surface peripheral edge 74 and a second end surface 76 extending between the second portion outer surface peripheral edge 72 and the second portion inner surface peripheral edge 74.

The first and second end surfaces 70, 76 are typically in a substantially face-to-face relationship relative to each other. When the lens first and second portions 32, 34 are selectively moved relative to each other between the portion contacting and spaced configurations shown respectively in FIGS. 12 and 11, the first and second end surfaces 70, 76 are respectively in a contacting and spaced relationship relative to each other.

As illustrated in FIGS. 7 and 11, when the first and second end surfaces 70, 76 are spaced apart from each other, the lens internal volume 56 can be further sub-divided into a substantially annular peripheral volume portion 78 extending between the first and second end surfaces 70, 76 and a central volume portion 80 extending radially centrally relative to the peripheral portion between the first and second portion inner surfaces 36, 40.

Typically, the attachment membrane 64 extends substantially between the first portion outer surface peripheral edge 66 and the second portion outer surface peripheral edge 72.

When the lens first and second portions 32, 34 are moved towards the portion contacting configuration shown in FIG. 12, the volume of the lens internal fluid 58 contained in the peripheral volume portion 78 is compressed towards the central volume portion 80, thereby increasing the overall pressure of the lens internal fluid and causing the IOL 10' to deform towards the accommodated configuration shown in FIGS. 8 and 12. Conversely, when the lens first and second portions 32, 34 are moved towards the portion spaced configuration shown in FIG. 11, the volume of the lens internal fluid contained in the central volume portion 80 is resiliently compressed by the first and second portion inner surfaces 36, 40 towards the peripheral volume portion 78 thereby decreasing the overall pressure of the lens internal fluid and causing the IOL 10' to deform towards the unaccommodated configuration.

The IOL 10' preferably includes a muscle-to-lens converting means attached thereto for converting a contraction of the ciliary muscle 28 into a movement of the first and second portions 32, 34 towards the contacting configuration shown in FIGS. 8 and 12. Preferably, the muscle-to-lens converting means includes at least one and preferably many haptics 82 extending substantially radially from the IOL 10.

Each haptic 82 defines an haptic distal end 84 for contacting the ciliary muscle 28. Each haptic 84 also includes an haptic biasing portion 86 for selectively contacting at least one of the first and second lens portions 32, 34 upon contraction of the ciliary muscle 28 and biasing the first and second portions 32, 34 towards the portion contacting configuration.

Typically, the haptic biasing portion 86 has a substantially forked configuration defining a pair of actuating tines 88. The actuating tines 88 are configured, sized and positioned so as to selectively contact the first and second lens portions 32, 34 and bias the first and second lens portions 32, 34 towards the portion contacting configuration upon contraction of the ciliary muscle 28.

Typically, the haptic biasing portion 86 further includes an anchoring tine 90 attached to the IOL 10'. The anchoring tine 90 is typically attached to the lens first portion 32 substantially adjacent to the first portion peripheral edge 48.

In use, the accommodative intra-ocular lenses 10 and 10' are adapted to be inserted in the human eye 12 typically using conventional surgery procedures or in the following manner. An ophthalmic surgeon typically first removes the natural crystalline lens by conventional methods, leaving an opening 92 in the anterior wall of the capsule 29. The accommodative intra-ocular lenses 10, 10' may then be folded into a compact size for insertion in a capsule 29 through such opening 92. Once inserted, the folded IOL 10 or 10' takes its unaccommodated shape inside the capsular bag. Alternatively, the IOL 10 or 10' is implanted in the capsular bag empty of its internal fluid 58 which is injected subsequently inside the empty IOL 10 or 10' to fill it inside the eye.

Implantation of the accommodative intra-ocular lenses 10 or 10' restores substantially normal vision by providing a highly refractive accommodative intra-ocular lens capable of bending light onto the retina 13. After implantation of the accommodative intra-ocular lenses 10 or 10' in a human eye 12, light refracts at the air-cornea interface in the same manner as the natural human eye. The light travels through the fluid-filled anterior chamber 18 and onto the accommodative intra-ocular lens 10 or 10'.

The configuration of the accommodative intra-ocular lens 10 or 10' changes in response to ciliary body or muscle movement, thus affecting the accommodative intra-ocular lens's refractive capabilities.

Hence, not only does the accommodative intra-ocular lenses 10 or 10' project an observed image on the retina, but they also accommodate in response to the action of the ciliary body. Indeed, those ordinarily skilled in the art will appreciate that the accommodative intra-ocular lenses 10 and 10' are operatively coupled with the ciliary muscle 28 to change shape in response to ciliary body movement.

In the case of the IOL 10 the main actuating effect is the increase in vitreous humor pressure caused by the contraction of the ciliary muscle 28 and transmitted to the internal fluid 58 by the lens second portion 34. In the case of the IOL 10' the main actuating effect is the decrease in circumlenticular space caused by the contraction of the ciliary muscle 26 converted into a movement of the first and second lens portions 32, 34 towards the portion contacting configuration. In both cases the contraction of the ciliary muscle 28 eventually causes an increase in internal fluid pressure that deforms the lens first portion 32 towards the accommodated configuration. In both cases, the configuration of the lens first portion 32 is such that refractive aberrations are minimized substantially throughout the range of accommodation.

The embodiments of the invention in which an exclusive privilege or property is claimed are defined as follows:

1. An accommodative intra-ocular lens, said accommodative intra-ocular lens being deformable between an unaccommodating configuration and an accommodating configuration, said accommodative intra-ocular lens being implantable within a mammalian eye including a retina, a ciliary muscle, a vitreous chamber located posteriorly towards said retina relatively to said lens said lens and a vitreous fluid contained within said vitreous chamber, said vitreous fluid defining a vitreous fluid pressure that increases upon contraction of said ciliary muscle and decreases upon relaxation of said ciliary muscle; said accommodative intra-ocular lens comprising:

a lens first portion and a lens second portion for being positioned respectively anteriorly and posteriorly relative to each other when said accommodative intra-ocular lens is inserted in said mammalian eye; said lens first portion defining a first portion inner surface and an opposed first portion outer surface and a first portion thickness extending therebetween; said lens second portion defining a second portion inner surface and an opposed second portion outer surface and a second portion thickness extending therebetween;

said lens first portion defining a substantially centrally disposed first portion central section and a first portion peripheral section extending radially from said first portion central section to a radially outwardmost first section peripheral edge; said first portion central and peripheral sections respectively defining a first central radius of curvature and a first peripheral radius of curvature and said first portion central section being relatively more easily deformable than said first portion peripheral section and said first portion thickness being substantially smaller about said first portion central section than about said first portion peripheral section, the first portion thickness increasing substantially gradually from said first portion central section to said first peripheral edge;

said lens second portion defining a substantially centrally disposed second portion central section and a second portion peripheral section extending radially from said second portion central section to a radially outwardmost second section peripheral edge; said second portion central and peripheral sections respectively defining a second central radius of curvature and a second peripheral radius of curvature;

said lens first and second portions being substantially sealingly joined together about their respective first and second portion peripheral edges and configured so as to define a lens internal volume therebetween;

said lens internal volume being filled with a substantially incompressible lens internal fluid; said lens internal fluid defining a variable internal fluid pressure exerted on said first and second portion inner surfaces;

said accommodative intra-ocular lens being configured such that both said first central radius of curvature and said first peripheral radius of curvature will decrease upon an increase in internal fluid pressure and both said first central radius of curvature and said first peripheral radius of curvature will increase upon a decrease in internal fluid pressure;

wherein said accommodative intra-ocular lens is deformable between said unaccommodating and accommodating configurations respectively upon the relaxation and contraction of said ciliary muscle and wherein the cross-sectional configuration of said first portion outer surface corresponds substantially to the equation: $y_o = \text{Log}_e (r_o^2 - x_o^2)^{0.5}$, wherein $r_o$ has approximately half the diameter value of the intra-ocular lens;

$x_o$ is a variable having a value where $r_o^2 - x_o^2 \geq 1$ and is determining an ordinate value of a locus of the cross-sectional configuration of the first portion outer surface;

$y_o$ is a variable determining an abscissa value of a locus of the cross-sectional configuration of the first portion outer surface and the cross-sectional configuration of said first portion inner surface corresponds substantially to the equation: $y_i = \text{Log}_e (r_i^2 - x_i^2)^{0.5}$, wherein $r_i$ has a smaller value than $r_o$ where $\text{Log}_e r_o - \text{Log}_e r_i$ represent said first portion central section thickness;

$x_i$ is a variable having a value where $r_i^2 - x_i^2 \geqq 1$ and is determining an ordinate value of a locus of the cross-sectional configuration of the first portion inner surface;

$y_i$ is a variable determining an abscissa value of a locus of the cross-sectional configuration of the first portion inner surface.

2. An accommodative intra-ocular lens as recited in claim 1, wherein the second portion thickness is substantially smaller about the second portion peripheral section than about the second portion central section.

3. An accommodative intra-ocular lens as recited in claim 2, wherein the second portion thickness increases substantially gradually from the second portion peripheral edge to the second portion central section.

4. An accommodative intra-ocular lens, said accommodative intra-ocular lens being deformable between an unaccommodating configuration and an accommodating configuration, said accommodative intra-ocular lens being implantable within a mammalian eye including a retina, a ciliary muscle, a vitreous chamber located posteriorly towards said retina relatively to said lens said lens and a vitreous fluid contained within said vitreous chamber, said vitreous fluid defining a vitreous fluid pressure that increases upon contraction of said ciliary muscle and decreases upon relaxation of said ciliary muscle; said accommodative intra-ocular lens comprising:

a lens first portion and a lens second portion for being positioned respectively anteriorly and posteriorly relative to each other when said accommodative intra-ocular lens is inserted in said mammalian eye; said lens first portion defining a first portion inner surface and an opposed first portion outer surface; said lens second portion defining a second portion inner surface and an opposed second portion outer surface;

said lens first portion defining a substantially centrally disposed first portion central section and a first portion peripheral section extending radially from said first portion central section to a radially outwardmost first section peripheral edge; said first portion central and peripheral sections respectively defining a first central radius of curvature and a first peripheral radius of curvature;

said first section peripheral edge includes
a first portion outer surface peripheral edge;
a first portion inner surface peripheral edge; and
a first end surface extending between said first portion outer surface peripheral edge and said first portion inner surface peripheral edge;

said lens second portion defining a substantially centrally disposed second portion central section and a second portion peripheral section extending radially from said second portion central section to a radially outwardmost second section peripheral edge; said second portion central and peripheral sections respectively defining a second central radius of curvature and a second peripheral radius of curvature;

said second section peripheral edge includes
a second portion outer surface peripheral edge;
a second portion inner surface peripheral edge; and
a second end surface extending between said second portion outer surface peripheral edge and said second portion inner surface peripheral edge; said first and second end surfaces being in a substantially face to face relationship relative to each other;

said lens first and second portions being sealingly attached together about their respective first and second portion peripheral edges by a portion attachment means to define a lens internal volume therebetween, the portion attachment means allowing said lens first and second portions to selectively move relative to each other between a portion contacting configuration and a portion spaced configuration wherein said first and second end surfaces are respectively in a contacting and spaced relationship relative to each other;

said lens internal volume being filled with a substantially incompressible lens internal fluid; said lens internal fluid defining a variable internal fluid pressure exerted on said first and second portion inner surfaces;

when said first and second end surfaces are spaced apart from each other, said lens internal volume includes
a substantially annular peripheral volume portion extending between said first and second end surfaces, and
a central volume portion extending radially centrally relative to said peripheral volume portion between said first and second portion inner surfaces;

whereby
when said lens first and second portions are moved towards said portion contacting configuration the volume of said lens internal fluid contained in said peripheral volume portion is compressed towards said central volume portion thereby increasing the overall pressure of said lens internal fluid and causing said accommodative intra-ocular lens to deform towards said accommodated configuration and,
when said lens first and second portions are moved towards said portion spaced configuration the volume of said lens internal fluid contained in said central volume portion is resiliently compressed towards said peripheral volume portion thereby decreasing the overall pressure of said lens internal fluid and causing said accommodative intra-ocular lens to deform towards said unaccommodated configuration;

said accommodative intra-ocular lens being configured such that both said first central radius of curvature and said first peripheral radius of curvature will decrease upon an increase in internal fluid pressure and both said first central radius of curvature and said first peripheral radius of curvature will increase upon a decrease in internal fluid pressure;

wherein said accommodative intra-ocular lens is deformable between said unaccommodating and accommodating configurations respectively upon the relaxation and contraction of said ciliary muscle.

5. An accommodative intra-ocular lens as recited in claim 4, wherein said portion attachment means includes an attachment membrane extending from said first portion outer surface peripheral edge to said second portion outer surface peripheral edge.

6. An accommodative intra-ocular lens as recited in claim 4 further comprising a muscle-to-lens converting means attached thereto for converting a contraction of said ciliary muscle into a movement of said first and second portions towards said portion contacting configuration.

7. An accommodative intra-ocular lens as recited in claim 6 wherein said muscle-to-lens converting means includes an haptic extending substantially radially from said accommodative intra-ocular lens; said haptic defining a distal end for contacting said cilliary muscle, said haptic including a biasing portion for selectively contacting at least one of said first and second lens portions upon contraction of said ciliary muscle and biasing said first and second portions towards said portion contacting configuration.

8. An accommodative intra-ocular lens as recited in claim 7 wherein said haptic biasing portion has a substantially forked configuration defining a pair of actuating tines, said actuating tines being configured, sized and positioned so as to selectively contact said first and second lens portions and bias said first and second lens portions towards said portion contacting configuration upon contraction of said ciliary muscle.

9. An accommodative intra-ocular lens as recited in claim 8 wherein said haptic biasing portion further includes an anchoring tine attached to said accommodative intra-ocular lens.

10. An accommodative intra-ocular lens as recited in claim 8 wherein said anchoring tine is attached to said lens first portion substantially adjacent to said first portion peripheral edge.

11. An accommodative intra-ocular lens as recited in claim 4, wherein a first portion thickness extends between said first portion inner surface and said opposed first portion outer surface and a second portion thickness extends between said second portion inner surface and said opposed second portion outer surface; and said first portion thickness is different about said first portion central section than about said first portion peripheral section and said second portion thickness is different about said second portion central section than about said second portion peripheral section.

12. An accommodative intra-ocular lens as recited in claim 11, wherein said first and second portion thicknesses are substantially smaller about said first and second portion central sections than about said first and second portion peripheral sections, respectively.

* * * * *